US00PP26256P2

(12) United States Plant Patent
Kamstra

(10) Patent No.: US PP26,256 P2
(45) Date of Patent: Dec. 22, 2015

(54) ***PHLOX* PLANT NAMED 'BARSEVENTYNINE'**

(50) Latin Name: *Phlox paniculata*
Varietal Denomination: Barseventynine

(71) Applicant: Silvan Kamstra, Aalsmeer (NL)

(72) Inventor: Silvan Kamstra, Aalsmeer (NL)

(73) Assignee: Bartels Stek B.V., Aalsmeer (NL)

( * ) Notice: Subject to any disclaimer, the term of this patent is extended or adjusted under 35 U.S.C. 154(b) by 142 days.

(21) Appl. No.: 13/999,079

(22) Filed: Jan. 10, 2014

(51) Int. Cl.
*A01H 5/00* (2006.01)

(52) U.S. Cl.
USPC ..... Plt./320

(58) Field of Classification Search
USPC ..... Plt./320
See application file for complete search history.

*Primary Examiner* — Annette Para
(74) *Attorney, Agent, or Firm* — C. A. Whealy

(57) ABSTRACT

A new and distinct cultivar of *Phlox* plant named Barseventynine, characterized by its upright and tall plant habit; vigorous growth habit; freely flowering habit; large pyramidal inflorescences with light red purple-colored flowers with darker red purple-colored centers; and good cut flower performance.

1 Drawing Sheet

Botanical designation: *Phlox paniculata.*
Cultivar denomination: 'BARSEVENTYNINE '.

BACKGROUND OF THE INVENTION

The present invention relates to a new and distinct cultivar of *Phlox* plant, botanically known as *Phlox paniculata* and hereinafter referred to by the name 'Barseventynine'.

The new *Phlox* plant is a product of a planned breeding program conducted by the Inventor in Aalsmeer, The Netherlands. The objective of the breeding program was to create new freely-flowering *Phlox* plants with unique and attractive flower colors.

The new *Phlox* plant originated from a cross-pollination made by the Inventor in 2008 in Aalsmeer, The Netherlands, of a proprietary selection of *Phlox paniculata* identified as code number 03-066-04, not patented, as the female, or seed, parent with a proprietary selection of *Phlox paniculata* identified as code number BS999, not patented, as the male, or pollen, parent. The new *Phlox* plant was discovered and selected by the Inventor as a single flowering plant from within the progeny of the stated cross-pollination in a controlled environment in Aalsmeer, The Netherlands in 2010.

Asexual reproduction of the new *Phlox* plant by cuttings in a controlled environment in Aalsmeer, The Netherlands since 2010 has shown that the unique features of this new *Phlox* plant are stable and reproduced true to type in successive generations.

SUMMARY OF THE INVENTION

Plants of the new *Phlox* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Barseventynine'. These characteristics in combination distinguish 'Barseventynine' as a new and distinct *Phlox* plant:

1. Upright and tall plant habit.
2. Vigorous growth habit.
3. Freely flowering habit.
4. Large pyramidal inflorescences with light red purple-colored flowers with darker red purple-colored centers.
5. Good cut flower performance.

Plants of the new *Phlox* and the parent selections differ primarily in the growth habit, inflorescence shape and flower color.

Plants of the new *Phlox* can be compared to plants of *Phlox paniculata* 'Bright Eyes', not patented. In side-by-side comparisons conducted in Aalsmeer, The Netherlands, plants of the new *Phlox* and 'Bright Eyes' differed in the following characteristics:

1. Plants of the new *Phlox* were taller than plants of 'Bright Eyes'.
2. Plants of the new *Phlox* flowered earlier than plants of 'Bright Eyes'.
3. Plants of the new *Phlox* and 'Bright Eyes' differed in inflorescence shape as plants of 'Bright Eyes' had more conical-shaped inflorescences.
4. Plants of the new *Phlox* and 'Bright Eyes' differed slightly in flower color.

BRIEF DESCRIPTION OF THE PHOTOGRAPH

The accompanying colored photograph illustrates the overall appearance of the new *Phlox* plant showing the colors as true as it is reasonably possible to obtain in colored reproductions of this type. Colors in the photograph may differ slightly from the color values cited in the detailed botanical description which accurately describe the colors of the new *Phlox* plant.

The photograph comprises a side perspective view of typical flowering stem of 'Barseventynine'.

DETAILED BOTANICAL DESCRIPTION

The aforementioned photograph and following observations, measurements and values describe plants grown during the late summer and early autumn in 17-cm containers in a glass-covered greenhouse in Aalsmeer, The Netherlands and under cultural practices typical of commercial cut flower *Phlox* production. During the production of the plants, day temperatures averaged 20° C. and night temperatures averaged 17° C. Plants were four months old when the photograph and description were taken. In the following description, color references are made to The Royal Horticultural Society Colour Chart, 2001 Edition, except where general terms of ordinary dictionary significance are used.

Botanical classification: *Phlox paniculata* 'Barseventynine'.

Parentage:

*Female, or seed, parent*.—Proprietary selection of *Phlox paniculata* identified as code number 03-066-04, not patented.

*Male, or pollen, parent*.—Proprietary selection of *Phlox paniculata* identified as code number BS999, not patented.

Propagation:

*Type*.—By cuttings.

*Root description*.—Fine, fibrous; white in color.

*Rooting habit*.—Freely branching; medium density.

Plant description:

*Plant and growth habit*.—Herbaceous perennial typically grown as a cut flower; upright and tall plant habit; vigorous growth habit.

*Plant height*.—About 70 cm.

*Plant width* (*spread*).—About 40 cm.

*Lateral branches*.—Length: About 70 cm. Internode length: About 5 cm. Strength: Strong. Aspect: Upright. Texture: Smooth, glabrous. Color: Close to 137C.

Leaf description:

*Arrangement*.—Opposite, simple.

*Length*.—About 15 cm.

*Width*.—About 5 cm.

*Shape*.—Ovate to elliptic.

*Apex*.—Acute.

*Base*.—Attenuate.

*Margin*.—Entire.

*Texture, upper and lower surfaces*.—Smooth, glabrous.

*Venation pattern*.—Pinnate.

*Color*.—Developing and fully expanded leaves, upper surface: Close to 137A; venation, close to 133A. Developing and fully expanded leaves, lower surface: Close to 137C; venation, close to 137C.

*Petioles*.—Length: About 2 mm. Diameter: About 2 mm. Texture, upper and lower surfaces: Smooth, glabrous. Color, upper and lower surfaces: Close to 59A.

Flower description:

*Flower type and flowering habit*.—Single rotate and salverform flowers arranged in compound terminal and lateral panicles; panicles roughly pyramidal in shape; flowers face mostly upright to outwardly; freely flowering habit with about 100 to 150 flowers developing per inflorescence.

*Fragrance*.—Moderately fragrant; sweet, pleasant.

*Natural flowering season*.—Plants begin flowering about ten to twelve weeks after planting; plants flower continuously during August and September in The Netherlands.

*Postproduction longevity*.—Flowers last about ten to twelve days as a cut flower; flowers not persistent.

*Flower buds*.—Height: About 2 cm. Diameter: About 5 mm. Shape: Ovate. Color: Close to 62D.

*Inflorescence height*.—About 15 cm.

*Inflorescence diameter*.—About 15 cm.

*Flower diameter*.—About 3 cm.

*Flower depth*.—About 2.5 cm.

*Petals*.—Quantity per flower: Typically five in a single whorl; petals fused at the base into a narrow tube. Length: About 1.3 cm. Lobe width: About 1.7 cm. Shape: Spatulate. Apex: Rounded. Margin: Entire. Texture, upper and lower surfaces: Smooth, glabrous. Color: When opening and fully opened, upper surface: Close to 65B; towards the throat, close to 67B. When opening and fully opened, lower surface: Close to 73D. Throat: Close to 74B. Tube: Close to 74B.

*Sepals*.—Quantity per flower: Typically five in a single whorl, fused towards the base; calyx, campanulate. Length: About 5 mm. Width: About 3 mm. Shape: Lanceolate. Apex: Narrowly acute. Margin: Entire. Texture, upper and lower surfaces: Smooth, glabrous. Color: When opening and fully opened, upper surface: Close to 137A. When opening and fully opened, lower surface: Close to 137C tinged with close to 60A.

*Peduncles*.—Length: About 5 cm. Diameter: About 2 mm. Strength: Moderately strong. Texture: Smooth, glabrous. Color: Close to 137A.

*Pedicels*.—Length: About 1 cm. Diameter: About 1 mm. Strength: Moderately strong. Texture: Smooth, glabrous. Color: Close to 59A.

*Reproductive organs*.—Stamens: Quantity per flower: Typically five; filaments fused with petals. Filament length: About 1.5 mm. Filament color: Close to 74B. Anther length: About 2 mm. Anther shape: Ovate. Anther color: Close to 8C. Pollen amount: Moderate. Pollen color: Close to 8C. Pistils: Quantity per flower: One. Pistil length: About 2.5 cm. Stigma shape: Cleft, three-parted. Stigma color: Close to 8D. Style length: About 2.5 cm. Style color: Light purple. Ovary color: Close to 60A and 137C.

*Seeds and fruits*.—Seed and fruit development have not been observed on plants of the new *Phlox*.

Garden performance: Plants of the new *Phlox* have been observed to have good garden performance and tolerate rain, wind and frost.

Disease & pest resistance: Plants of the new *Phlox* have been observed to be relatively tolerant to Powdery Mildew; plants of the new *Phlox* have not been observed to be resistant to pests and pathogens common to *Phlox* plants.

It is claimed:

1. A new and distinct *Phlox* plant named 'Barseventynine' as illustrated and described.

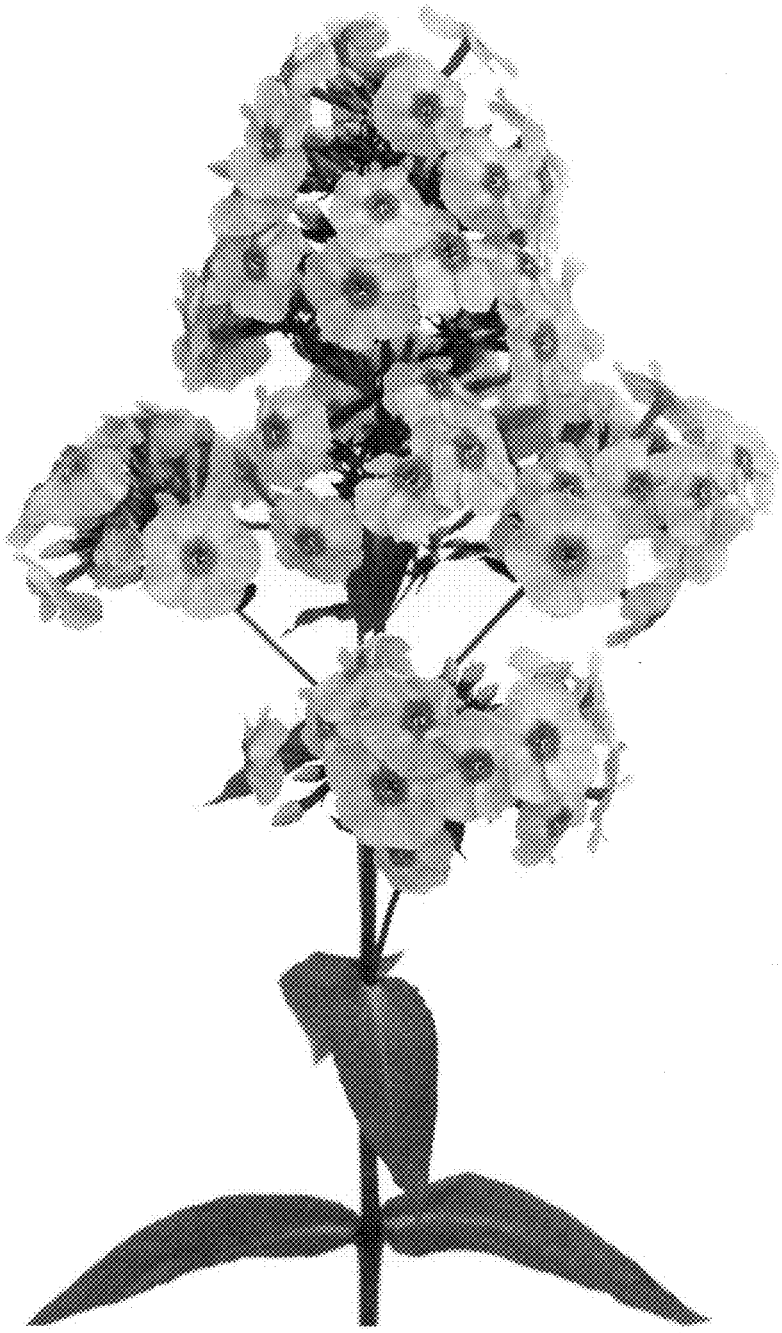

* * * * *